(12) United States Patent
Farone et al.

(10) Patent No.: US 9,102,610 B2
(45) Date of Patent: Aug. 11, 2015

(54) PROCESS FOR PREPARING LIQUID OVERBASED METAL CARBOXYLATES, MIXED METAL STABILIZERS CONTAINING SAME, AND STABILIZED HALOGEN-CONTAINING POLYMERS THEREWITH

(75) Inventors: Eric V. Farone, Hudson, OH (US); Benjamin P. Labovitz, Valparaiso, IN (US); Nicholas A. Kruse, Griffith, IN (US)

(73) Assignee: AM Stabilizers Corporation, Hammond, IN (US)

( * ) Notice: Subject to any disclaimer, the term of this patent is extended or adjusted under 35 U.S.C. 154(b) by 891 days.

(21) Appl. No.: 13/306,308

(22) Filed: Nov. 29, 2011

(65) Prior Publication Data
US 2013/0137806 A1 May 30, 2013

(51) Int. Cl.
*C07C 51/00* (2006.01)
*C07C 51/41* (2006.01)
*C08K 5/098* (2006.01)
*C08K 5/00* (2006.01)

(52) U.S. Cl.
CPC .......... *C07C 51/414* (2013.01); *C08K 5/0091* (2013.01); *C08K 5/098* (2013.01)

(58) Field of Classification Search
CPC ...... C08L 57/08; C08K 5/098; C08K 5/0091; C07C 57/12; C07C 51/414
See application file for complete search history.

(56) References Cited

U.S. PATENT DOCUMENTS

| | | | |
|---|---|---|---|
| 2,616,904 A | 11/1952 | Asseff et al. | |
| 2,760,970 A | 8/1956 | Le Suer et al. | |
| 2,767,164 A | 10/1956 | Asseff et al. | |
| 2,798,852 A | 7/1957 | Wiese et al. | |
| 2,802,816 A | 8/1957 | Asseff et al. | |
| 3,027,325 A | 3/1962 | McMillen et al. | |
| 3,031,284 A | 4/1962 | Andress | |
| 3,342,733 A | 9/1967 | Robbins et al. | |
| 3,533,975 A | 10/1970 | Scullin | |
| 3,773,664 A | 11/1973 | Lesuer | |
| 3,779,992 A | 12/1973 | Liu et al. | |
| 4,665,117 A | 5/1987 | Quinn | |
| 5,830,935 A | 11/1998 | Khattar et al. | |
| 5,859,267 A | 1/1999 | Khattar et al. | |
| 2004/0102555 A1* | 5/2004 | Fakinlede et al. | 524/386 |

FOREIGN PATENT DOCUMENTS

WO 2005040305 5/2005

OTHER PUBLICATIONS

"Notification of Transmittal of the International Search Report and Written Opinion of the International Searching Authority, or the Declaration" regarding PCT/US2012/020918 filed Jan. 11, 2012. International Searching Authority. Notification received Mar. 26, 2012.

* cited by examiner

*Primary Examiner* — Peter D Mulcahy
(74) *Attorney, Agent, or Firm* — Wood, Herron & Evans, LLP

(57) ABSTRACT

Liquid overbased alkali or alkaline earth metal carboxylates, particularly barium carboxylates, are prepared by a process which includes the use of a beta diketone as a reaction promoter during carbonation. Mixed metal stabilizers containing the overbased metal carboxylates are used as stabilizers for halogen-containing polymers such as polyvinyl chloride (PVC).

22 Claims, No Drawings

PROCESS FOR PREPARING LIQUID OVERBASED METAL CARBOXYLATES, MIXED METAL STABILIZERS CONTAINING SAME, AND STABILIZED HALOGEN-CONTAINING POLYMERS THEREWITH

FIELD OF THE INVENTION

The present invention relates to a process for producing liquid overbased alkali or alkaline earth metal carboxylates, particularly barium carboxylates. Mixed metal stabilizers containing the overbased metal carboxylates are used as stabilizers for halogen-containing polymers such as polyvinyl chloride (PVC).

BACKGROUND OF THE INVENTION

The preparation of overbased calcium or barium salts of carboxylic acids with alkyl phenols is disclosed in the following U.S. Pat. Nos. 2,616,904; 2,760,970; 2,767,164; 2,798,852; 2,802,816; 3,027,325; 3,031,284; 3,342,733; 3,533,975; 3,773,664; 3,779,992; 4,665,117; 5,830,935; and 5,859,267. The use of these overbased metal salts in halogen-containing polymers is also described in the aforementioned patents. Furthermore, these prior art patents also discuss the use of alkyl phenol as a promoter in the manufacture of the overbased metal salts.

According to the teachings of U.S. Pat. Nos. 4,665,117 and 5,859,267, for example, alkali or alkaline earth metal salts are prepared where alkyl phenol is used as a promoter of the reaction. However, alkyl phenol is also a major cause for the development of color in the final product and in stabilized PVC compositions. These patents also address the color stability issues of over-based alkyl phenates by applying propylene oxide, alkyl glycidyl esters, phosphites, and other such additives to restrict the formation of colored species which detract from the applications where a light-colored polymer product is desired. However, a number of disadvantages associated with the toxic nature of propylene oxide as a color inhibitor have been documented. Furthermore, due to recent legislation, primarily in Europe and Asia, with the accompanying impact on U.S. suppliers, there exists a need for a phenol-free overbased metal carboxylate. Also, environmental concerns with existing polymer stabilizers have stimulated interest in alternative stabilizers for the replacement of heavy metal stabilizers. As part of the voluntary initiative of Vinyl 2010, the European Vinyl Industry (EVI) is also committed to replacing heavy metal stabilizers and overcoming toxicity in all PVC applications by 2015. Thus, there has been considerable interest in making phenol and alkyl-phenol free PVC stabilizers, especially overbased metal stabilizers, and developing a new generation of environmentally acceptable PVC stabilizers that prevent degradation and change in color during processing, and also provide tangible benefits to the manufacture of useful articles.

SUMMARY OF THE INVENTION

The present invention relates to a process for preparing a liquid overbased alkali or alkaline earth metal salt of carboxylic acid. The process involves reacting a mixture of the metal base and a carboxylic acid with an excess of metal base to carboxylic acid, and carbonating the reaction mixture to produce the overbased metal carbonate. It has been discovered that beta diketones provided during carbonation of the reaction mixture produce desirable overbased alkali or alkaline earth metal salts having high levels of basicity, for example 20 to 40% barium or calcium. The beta diketones perform as well as the alkyl phenols as promoters of the reaction to produce overbased metal salts under typical commercial preparation techniques. The method of this invention allows for the production of the overbased alkaline earth metal carbonates in the complete absence of phenolic compounds. For example, 1,3-diketones such as dibenzoyl methane, stearoyl benzoyl methane, octanoyl benzoyl methane, and acetyl acetone have been successfully employed in the production of the desired overbased metal salts.

This invention enables the production of phenol-free overbased barium or calcium carboxylates having high levels of metal up to 40% by weight or in the range of 25 to 40% by weight. Moreover, the addition of a color inhibitor is unnecessary in order to provide a lighter colored product for use in the stabilization of PVC. In particular, the overbased barium salts possess performance advantages which, up to this point, have only been achieved commercially with the use of alkyl phenols as a promoter. Therefore, the performance advantages associated with overbased barium salts such as low plate-out, excellent color-hold, long-term heat stability performance, compatibility with stabilizer components, etc., are achievable by employing the products of this invention.

Among other benefits, this invention meets the requirements of recent legislation, primarily in Europe and Asia, directed to environmentally acceptable PVC stabilizers which prohibit phenols or phenol derivatives in plastics or polymers. Plant workers, formulators, and customers benefit from this invention because they will not be exposed to the adverse effect of phenols and other additives such as propylene oxide, which have been employed in the production and use of overbased salts. Moreover, the heat stability of PVC compositions which employ the overbased carboxylates of this invention is equivalent to or better than the stabilities achieved with overbased phenates produced according to prior art techniques.

The above advantages, benefits, and further understanding of this invention will be apparent with reference to the following detailed description and preferred embodiments.

DETAILED DESCRIPTION OF THE INVENTION AND PREFERRED EMBODIMENTS

A. Liquid Overbased Alkali or Alkaline Earth Metal Salts of Beta Diketone/Carboxylic Acid.

The present invention relates to a shelf-stable liquid overbased alkali or alkaline earth metal salt of a beta diketone and carboxylic acid. These liquid salts are referred to herein sometimes as "diketonate/carboxylate" because both the beta diketone and carboxylic acid enter into the reaction to produce shelf-stable liquids containing an alkaline earth metal carbonate such as calcium or barium carbonate, and a mixture of a metal diketonate and carboxylate (hereinafter "diketonate/carboxylate"). These liquids are referred to sometimes hereinafter more simply as "overbased alkali or alkaline earth metal salt(s)", "overbased metal salt(s)", or "overbased alkaline earth metal carboxylate/carbonate(s)". Liquid overbased calcium and barium salts, in a preferred form of the invention, are essentially free of a phenol or phenolic derivative. The process for preparing a shelf-stable liquid of an overbased alkaline earth metal salt of a beta diketone/carboxylic acid involves reacting the alkaline earth metal base and the acid with an equivalent ratio of metal base to the combination of the beta diketone and acid being greater than 1:1 to make a basic product in the presence of a liquid hydrocarbon. An aliphatic alcohol may be employed in the reaction. The mixture is acidified, preferably by carbonation, and water is removed from the reaction product to obtain a shelf-stable liquid overbased alkaline earth metal salt.

It has been found, and this invention is predicated in part upon, providing during carbonation a 1,3-diketone, which reacts at commercial rates as a promoter or reactant to produce the overbased metal salts having up to about 40% by weight, usually about 20 to 40% by weight, of the overbased calcium or barium metal. Up to the discoveries made in accordance with this invention, it was not considered possible to make in a practical commercial operation, a highly overbased barium carboxylate/carbonate, for example, that may be filtered at commercial or practical rates which was free of phenol or phenolic derivatives.

In one preferred form of the invention, the shelf-stable liquid of an overbased barium salt of a beta diketone/fatty acid comprises a barium carbonate, a barium beta diketonate/carboxylate of the fatty acid, a liquid hydrocarbon, and an aliphatic alcohol, with the liquid being free of a phenol or a phenolic derivative.

The fatty acid of the overbased liquid salt is generally a $C_{12}$-$C_{22}$ fatty acid, including, for example, lauric, pyristic, palmitic, stearic, and behenic, among the saturated fatty acids. Unsaturated fatty acids include palmitoleic, oleic, linoleic, and linolenic. Among these fatty acids, oleic is presently preferred in preparing the overbased liquid carboxylates. The alkaline earth metal of the salt is selected from the group consisting of calcium, barium, magnesium, and strontium. Alkali metals include sodium, potassium, and lithium. For example, shelf-stable liquids of overbased calcium and barium oleates have been prepared. These overbased barium salts, for example, contain barium carbonate, barium oleate, barium diketonate, a liquid hydrocarbon diluent, and an aliphatic alcohol.

B. 1,3-Diketone Compound

The 1,3-diketone compound employed in this invention is one of a class of known 1,3-diketones having a cyclic or open chain of 5 to 30 carbon atoms represented by the formula:

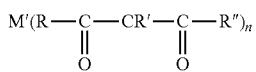

When in this formula M' is a hydrogen atom, the formula becomes

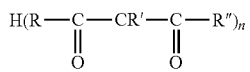

which is a way to indicate by a single expression that the hydrogen atom can be linked in more than one way, as in the tautomeric formulas I to III (i.e. formulas of compounds in readily movable equilibrium with one another)

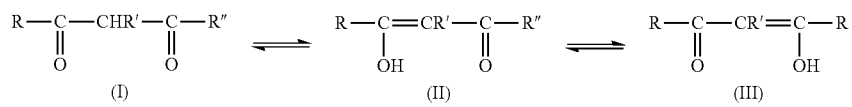

the latter two of which are identical when R and R" are the same and non-identical when R and R" are different. The relative proportions of tautomers I, II, and III in the 1,3-diketone compounds is a function of the identity or R and R"; for example the enol content (i.e. combined content of the C=C containing tautomers II and III) has been reported as 76.4% for diacetylmethane (R=R"=methyl) and 89.2% for acetylbenzoylmethane (R=methyl, R"=phenyl) (see A. Gero, J. Organic Chem. 1954, vol. 19, p. 1960-1970). See also U.S. Pat. No. 4,252,698, which is incorporated herein by reference.

Hydrocarbon groups, R, R', and R", can be open chain or cyclic and include such aliphatic, cycloaliphatic, and aromatic hydrocarbon groups as alkyl and alkenyl groups having 1 to 18 carbon atoms, cycloalkyl, cycloalkenyl and cycloalkylalkylene, and alkylcycloalkyl groups having 5 to 18 carbon atoms, and non-condensed aryl groups (including aralkyl and alkyaryl) having 6 to 18 carbon atoms, for example methyl, ethyl, propyl, isopropyl, isobutyl, n-butyl, s-butyl, t-butyl, 1-pentyl, 3-pentyl, 1-hexyl, 1-heptyl, 3-heptyl, 1-octyl, 2,4,4-trimethylpentyl, t-octyl, nonyl, decyl, tridecyl, pentadecyl, heptadec-8-en-1-yl, n-octadecyl, allyl, methallyl, 2-hexenyl, 1-methylcyclopentyl, cyclohexyl, cyclohexanepropyl, phenyl, m-tolyl, p-ethylphenyl, t-butylphenyl, benzyl, phenylpropyl and nonylbenzyl. R' as well as either but not both of R and R" can be hydrogen. When the groups R and R' are linked to form an oxygen-heterocyclic ring, the 1,3-diketone compound can be for example dehydroacetic acid, dehydropropionylacetic acid, and dehydrobenzoylacetic acid. When the groups R and R' are linked to form a carbocyclic ring, the 1,3-diketone compound can be for example 2-acetyl-1-tetralone, 1-palmitoyl-2-tetralone, 2-stearoyl-1-tetralone, 2-benzoyl-1-tetralone, 2-acetyl-cyclohexanone, and 2-benzoylcyclohexanone. When the groups R and R" are linked to form a carbocyclic ring, the 1,3-diketone compound can be for example cyclopentane-1,3-dione, cyclohexane-1,3-dione, 5,5-dimethylcyclohexane-1,3-dione, 2,2'-methylenebis(cyclohexane-1,3-dione), and 2-acetylcyclohexane-1,3-dione. When R, R' and R" are discrete groups, the 1,3-diketone compound can be, for example, benzoyl-p-chlorobenzoylmethane, bis(4-methyl-benzoyl)methane, bis(2-hydroxybenzoyl)methane, benzoylacetylmethane, tribenzoylmethane, diacetylbenzoylmethane, stearoyl-benzoylmethane, palmitoyl-benzoylmethane, lauroylbenzoylmethane, dibenzoyl methane, 4-methoxybenzoyl-benzoylmethane, bis(4-methoxybenzoyl)methane, bis(4-chlorobenzoyl)methane, bis(3,4-methylenedioxybenzoyl)methane, benzoyl-acetyl-octylmethane, benzoyl-acetyl-phenylmethane, stearoyl-4-methoxybenzoylmethane, bis(4-t-butylbenzoyl)methane, benzoyl-acetyl-ethylmethane, benzoyl-trifluoroacetyl-methane, diacetylmethane, butanoyl-acetylmethane, heptanoyl-acetylmethane, triacetylmethane, stearoylacetylmethane, palmitoyl-acetylmethane, lauroyl-acetylmethane, benzoyl-formylmethane, acetyl-formyl-methylmethane, benzoyl-phenylacetylmethane, bis(cyclohexane-carbonyl)methane, and dipivaloylmethane.

C. Amounts of Reactants and Catalysts

The amount of alkali or alkaline earth metal base utilized in the preparation of basic salts is an amount which is more than one equivalent of the base per equivalent of the combined diketone/carboxylic acid or organic moiety, and more generally, will be an amount sufficient to provide at least three equivalents of the metal base per equivalent of the diketone and acid. The alcohols that are used include any one of the various available substituted or unsubstituted aliphatic or cycloaliphatic alcohols containing from 1 to about 20 or more carbon atoms. The amount of the beta diketone and optionally the alcohol included in the mixture is not critical. The beta diketone promoter is included in the mixture to contribute to the utilization of the carbon dioxide gas during treatment of the mixture with the acidic gas. Generally, at least about 0.1 equivalent and preferably from about 0.05 to about 10 equivalents of the beta diketone (and the alcohol if present) per equivalent of a monocarboxylic acid is employed. Larger amounts, for example, up to about 20 to about 25 equivalents of alcohol and beta diketone may be used, especially in the case of lower molecular weight alcohols. Water, which may optionally also be present in the mixture, may be present as water added as such to the mixture, or the water may be present as "wet alcohol", "wet" beta diketone, hydrates of the alkali or alkaline earth metal salts, or other types of chemically combined water with the metal salts.

In addition to the components described above, the reaction mixtures used to prepare the basic metal salts ordinarily will contain a diluent. Generally, any hydrocarbon diluent can be employed, and the choice of diluent is dependent in part on the intended use of the mixture. Most generally, the hydrocarbon diluent will be a non-volatile diluent such as the various natural and synthetic oils of lubricating viscosity.

The amount of basic alkali or alkaline earth metal base utilized in the preparation of basic salts is an amount which is more than one equivalent of the base per equivalent of beta diketones and acid, and more generally, will be an amount sufficient to provide at least three equivalents of the metal base per equivalent of the acid and beta diketone. Larger amounts can be utilized to form more basic compounds, and the amount of the metal base included may be any amount up to that amount which is no longer effective to increase the proportion of metal in the product. When preparing the mixture, the amount of beta diketone and the optional alcohol included in the mixture is not critical except that the ratio of equivalents of monocarboxylic acid to beta diketone should be at least about 1.1:1, that is, the monocarboxylic acid is present in excess with respect to the beta diketone. The ratio of equivalents of the metal base of the combination of the other components in mixture should be greater than 1:1 in order to provide a basic product. More generally, the ratio of equivalents will be at least 3:1.

The step of carbonation involves treating the mixtures described above with $CO_2$ gas in the absence of free oxygen until the titratable basicity is determined using phenolphthalein. Generally, the titratable basicity is reduced to a base number below about 10. The mixing and carbonation steps of the present invention require no unusual operating conditions other than preferably the exclusion of free oxygen. The base, fatty acid, beta diketone, and liquid hydrocarbon are mixed, generally heated, and then treated with carbon dioxide as the acidic gas, and the mixture may be heated to a temperature which is sufficient to drive off some of the water contained in the mixture. The treatment of the mixture with the carbon dioxide preferably is conducted at elevated temperatures, and the range of temperatures used for this step may be any temperature above ambient temperature up to about 325° F., and more preferably from a temperature of about 130° F. to about 325° F. Higher temperatures may be used, but there is no apparent advantage in the use of such higher temperatures. Ordinarily, a temperature of about 130° F. to 325° F. is satisfactory.

D. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C=CHCl$ to polyvinyl chloride ($CH_2CHCl-$) wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

Metal compound heat stabilizers of vinyl halide resin compositions are well known. These metal compounds serve to capture HCl liberated during heat processing of the vinyl halide resin composition into its final shape. The metal can be lead, cadmium, barium, calcium, zinc, strontium, bismuth, tin, or antimony, for example. The stabilizers are usually metal salts of a carboxylic acid, advantageously of a $C_8$-$C_{24}$ carbon chain link monocarboxylic acid such as lauric, oleic, stearic, octoic, or similar fatty acid salts. Mixed metal salts of such acids, and their preparation, are familiar to those skilled in the art to which this present invention pertains. Mixed metallic carboxylates involving calcium/zinc or barium/zinc blends alone and in combination with other stabilizers or additives such as beta-diketones, phosphite salts and phenolic antioxidants have been used. The metal stabilizer is a mixed metal salt of a carboxylic acid. Mixed metal salts of such acids, and their preparation, are also familiar to those skilled in the art to which this present invention pertains.

E. End Uses for the Stabilizers

The liquid stabilizers or mixed metal stabilizers of this invention may be used in a number of end products. Examples include: wall covering, flooring (vinyl tile and inlay), medical devices, dip coating, chair mat, banner film, pigment dispersion, vinyl siding, piping, fuel additive, cosmetic, ceiling tile, roofing film, wear layer, play balls or toys, teethers, fencing, corrugated wall panels, dashboards, and shifter boots.

The following Examples illustrate the preparation of the shelf stable haze free liquids of the overbased salts in accordance with the method of the present invention, but these examples are not considered to be limiting the scope of this invention. Unless otherwise indicated in the following examples and elsewhere in the specification and claims, all parts and percentages are by weight, and all temperatures are in degrees fahrenheit.

COMPARATIVE EXAMPLE 1

The following ingredients and amounts were employed in this Comparative Example to demonstrate the normal procedure which has been employed to make a barium nonylphenate overbased salt.

| Ingredients | Amount (g) |
|---|---|
| Oleic Acid | 58.3 |
| 1418 Alcohol | 35 |
| 100 Neutral Oil | 101.5 |
| Nonyl Phenol | 30 |
| BaOH | 248 |

The 1418 alcohol is a commercially available mixture of aliphatic alcohols containing 14-18 carbon atoms, and the neutral oil is a mineral oil.

The oleic acid, oil, and alcohol ingredients were charged into a reaction vessel and mixed at room temperature while purging the vessel with nitrogen gas at 2 liters per minute. After a period of about 15-20 minutes, the mixture was heated while stirring to a temperature of about 133° F. At about 133° F., the BaOH was incrementally added in three separate additions of about 83, 81, and 84 grams each. At about 138° F., 2 drops of anti-foam were added to the reaction mixture. Thereafter, the reaction mixture was heated over about an hour to a temperature of about 240° F., whereupon the nonyl phenol was charged to the reaction mixture. After a period of about 10-15 minutes at a temperature of about 240° F., the reaction mixture was heated to about 265° F. During the course of the reaction, water was removed. After all of the nonyl phenol was charged, the nitrogen purge was stopped, and the mixture was carbonated with carbon dioxide at a rate of about 1 liter per minute for approximately 4.5 hours. 18 mls of water were removed during the course of the reaction, and the resulting product was a filterable hot solution which titrated to 33.19% barium.

EXAMPLE II

The objective of this example was to prepare an overbased barium 1,3-diketonate/monocarboxylate of this invention. This is achieved by replacing the nonyl phenol of Comparative Example 1 with an equivalent amount of dibenzoyl methane. For this purpose, the following ingredients and their actual amounts were employed.

| Ingredients | Amount (g) |
|---|---|
| Oleic Acid | 54.5 |
| 1418 Alcohol | 35.1 |
| 100 Neutral Oil | 101.5 |
| Dibenzoyl Methane | 35 |
| BaOH | 245.1 |

The procedure of Comparative Example I was followed, after substituting dibenzoyl methane for the nonyl phenol to make the overbased barium diketonate/oleate carbonate salt. Approximately the same time table of Example I for mixing the reaction ingredients, heating and charging of the barium hydroxide and dibenzoyl methane were used at approximately the same temperatures, except the carbonation step was conducted at about 310° F. for about 3.5 hours. About 21 mls of water was recovered and the storage-stable liquid of the overbased barium salt was prepared. The storage-stable liquid titrated to a barium content of about 29.49%.

EXAMPLE III

In this Example, octanoyl benzoyl methane was substituted for the nonyl phenol in Comparative Example I, and the following ingredients were employed.

| Ingredients | Amount (g) |
|---|---|
| Oleic Acid | 54.5 |
| 1418 Alcohol | 35.1 |
| 100 Neutral Oil | 101.6 |
| Octanoyl benzoyl methane | 33.5 |
| BaOH | 244.8 |

Following the procedure of Comparative Example I, the reaction ingredients were charged to their reaction vessel and over similar reaction times and temperatures, the liquid overbased barium salt of the diketonate/oleate carbonate was prepared, except carbonation was conducted at about 253° F. for about 3 hours. During the course of the reaction about 18.5 mls of water were removed, and the resulting storage-stable liquid was formed and filtered to a honey color, which titrated to barium in an amount of 29.39%.

EXAMPLE IV

In this Example stearoyl benzoyl methane was substituted for the nonyl phenol of Comparative Example I and the following ingredients were employed.

| Ingredients | Actual (g) |
|---|---|
| Oleic Acid | 54.5 |
| 1418 Alcohol | 35.1 |
| 100 Neutral Oil | 101.5 |
| Stearoyl benzoyl methane | 52.6 |
| BaOH | 245.2 |

Following the same procedure of Comparative Example I, after carbonation at about 260° F. for about 3 hours, and removal of about 16.5 mls of water, liquid barium diketonate/oleate carbonate was prepared that titrated to 23.22% barium.

EXAMPLE V

In order to demonstrate the heat-stabilizing effectiveness of the basic alkaline earth metal organic salts of this invention, the products of Examples 2-3 were formulated as stabilizers for PVC and designated hereinafter as "Stabilizer C, D, E, and F" with reference to the following Table I.

TABLE I

| Ingredient | A | B | C | D | E | F |
|---|---|---|---|---|---|---|
| PLASTISTAB 2508 | 21 | 21 | | | | |
| Example 2 Product | | | 24.5 | 24.5 | | |
| Example 3 Product | | | | | 21 | 21 |
| Diphenyl isodecyl phosphite | 35 | 35 | 35 | 35 | 35 | 35 |
| 22% zinc octoate | 7 | 7 | 7 | 7 | 7 | 7 |
| Benzoic acid | 2 | 2 | 2 | 2 | 2 | 2 |
| Oleic acid | 2 | 2 | 2 | 2 | 2 | 2 |
| Anox 10% | 1 | 1 | 1 | 1 | 1 | 1 |
| Hydrocarbon solvent | 29 | 32 | 25.5 | 28.5 | 29 | 32 |
| Dibenzoyl methane | 3 | — | 3 | — | 3 | — |

With reference to Table I, commercially available 34% overbased barium nonyl phenate, sold by Halstab as PLAS- TISTAB 2508, was formulated into a stabilizer composition designated "Stabilizers A and B" as controls for purposes of demonstrating the heat-stabilizing effectiveness of the overbased metal salts of this invention as compounded stabilizers for PVC. The stabilizer compositions A through F were each formulated in a standard polyvinyl chloride (PVC) formulation at a level of 3 parts where the balance of the formulation included 100 parts of polyvinyl chloride. The PVC formulation was milled at 365° F. for five minutes, and static heat stability was determined at 375° F. and 400° F. Over a period of about 40 minutes, heat stabilizing effectiveness of the compositions A-F were measured by color change. Color change was measured by a colorimeter as an indication of yellowing. The details of the color values obtained by Stabilizers A-F are shown in the following Tables II and III.

TABLE II (375° F.)

| Stabi-lizer | Time (Minutes) | | | | | | | | |
|---|---|---|---|---|---|---|---|---|---|
| | 0 | 5 | 10 | 15 | 20 | 25 | 30 | 35 | 40 |
| A | 3.79 | 3.86 | 4.23 | 4.74 | 4.96 | 8.81 | 10.36 | 11.64 | 12.20 |
| B | 11.09 | 13.03 | 15.42 | 19.00 | 18.67 | 18.67 | 17.82 | 16.82 | 15.18 |
| C | 3.52 | 3.68 | 3.96 | 4.62 | 4.89 | 6.69 | 7.81 | 9.29 | 9.69 |
| D | 11.08 | 13.55 | 17.11 | 20.55 | 20.83 | 21.03 | 20.07 | 17.66 | 16.18 |
| E | 3.39 | 3.48 | 3.90 | 4.48 | 4.78 | 6.36 | 7.77 | 8.76 | 9.66 |
| F | 5.54 | 6.38 | 8.86 | 13.91 | 15.38 | 16.11 | 15.85 | 15.04 | 14.22 |

TABLE III (400° F.)

| Stabilizer | 0 | 5 | 10 | 15 | 20 | 25 | 30 |
|---|---|---|---|---|---|---|---|
| A | 3.64 | 4.17 | 5.48 | 10.39 | 12.24 | 21.94 | 3.06 |
| B | 10.95 | 14.23 | 16.94 | 15.12 | 13.56 | 1.44 | 0 |
| C | 3.50 | 3.96 | 5.10 | 8.51 | 11.98 | 0.03 | 0 |
| D | 10.99 | 16.27 | 19.79 | 16.07 | 13.73 | 23.85 | 2.53 |
| E | 3.39 | 3.81 | 4.95 | 8.34 | 13.31 | −0.78 | 0 |
| F | 5.51 | 7.51 | 13.46 | 13.13 | 12.35 | 20.82 | 2.23 |

The color b values were determined by ASTM E313-73. The color values as measured by a colorimeter as an indication of yellowing included heat chips, which demonstrated the appearance of the milled PVC and stabilized compositions.

Both the colorimeter color values shown by Tables II and III and the heat chip charts demonstrated the equivalent effectiveness of the basic alkaline earth metal organic salts of this invention by a comparison of the performance of the stabilizer compositions C-F with the commercially available basic barium salts of stabilizer compositions A-B. For instance, the comparison with stabilizers A-B demonstrated that heat stability was improved with the product of this invention, notwithstanding the absence of the phenolic component. In other words, the basic barium metal carbonates of the 1,3-diketone and oleic acid exemplified by dibenzoyl methane or octanoyl dibenzoyl methane provided an equivalent or better result in heat-stabilizing effectiveness, upon comparison with the barium metal alkyl phenate that is commercially available. An additional benefit, as demonstrated by the heat-stabilizing data, is that a color inhibitor is not necessary in order to achieve a light-colored commercial product. Further advantages are obtained because plant workers, customers, or users of the compositions are not exposed to phenol or derivatives of phenol, as developed in the Summary of this invention.

Surprisingly, overbased barium organic salts having a high percentage of barium are achievable according to the process of this invention, such that levels of barium on the order of about 20 to about 40% are achievable in the overbased compound, thereby achieving heat-stabilizing effectiveness equivalent to or better than the effectiveness achieved by presently available overbased barium salts.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall with the scope of the invention.

What is claimed is:

1. A process for preparing a phenol-free storage-stable liquid overbased alkali or alkaline earth metal salt comprising:
   reacting a mixture of an alkali or alkaline earth metal base and a carboxylic acid with an equivalent ratio of metal base to carboxylic acid being greater than 1:1 in the presence of liquid hydrocarbon, and
   carbonating the reaction mixture in the presence of a 1,3-diketone which acts as a promoter of the reaction during carbonation in the absence of any phenol or phenolic derivative to produce the phenol-free storage-stable liquid overbased alkali or alkaline earth metal salt.

2. The process of claim 1 wherein the carboxylic acid is an aliphatic or aromatic carboxylic acid and the 1,3-diketone has a cyclic or open chain of 5 to 30 carbon atoms.

3. The process of claim 2 wherein said carboxylic acid is a C12-C22 fatty acid.

4. The process of claim 3 wherein said fatty acid is oleic acid.

5. The process of claim 1 wherein said alkaline earth metal is selected from the group consisting of calcium, barium, magnesium, and strontium.

6. The process of claim 1 wherein the alkali metal is selected from the group consisting of sodium, potassium, and lithium.

7. The process of claim 1 wherein said alkaline earth metal is barium.

8. The process of claim 7 wherein the overbased salt is a barium oleate/ketonate/carbonate.

9. The process of claim 1 wherein the amount of alkali or alkaline earth metal in the salt is about up to 40% by weight.

10. The process of claim 1 wherein the amount of alkali or alkaline earth metal in the salt is about 25% to about 40% by weight.

11. The process of claim 1 wherein the reaction is conducted in the presence of alcohol.

12. A process for preparing a phenol-free storage-stable liquid overbased barium salt free from any phenol or phenolic derivative comprising
   reacting a barium hydroxide and a carboxylic acid with an equivalent ratio of barium hydroxide to carboxylic acid being greater than 1:1 in the presence of liquid hydrocarbon, carbonating the reaction mixture in the presence of a 1,3-diketone which acts as a promoter of the reaction during carbonation to produce the overbased barium salt and byproduct water in the absence of any phenol or phenolic derivative, and
   removing water from the reaction product to provide the phenol-free storage-stable liquid overbased barium carboxylate/1,3-diketonate/carbonate.

13. The process of claim 12 wherein the 1,3-diketone is selected from the group consisting of dibenzoyl methane, stearoyl benzoyl methane, and octanoyl benzoyl methane.

14. The process of claim 12 wherein said organic acid is an aliphatic or aromatic carboxylic acid.

15. The process of claim 14 wherein said carboxylic acid is a C12-C22 fatty acid.

16. The process of claim 15 wherein said fatty acid is oleic acid.

17. The process of claim 12 wherein the amount of alkali or alkaline earth metal in the salt is about up to 40% by weight.

18. The process of claim 12 wherein the reaction is conducted in the presence of alcohol.

19. The liquid overbased alkali or alkaline earth metal salt of the 1,3-diketone and carboxylic acid prepared in accordance with the process of claim 1.

20. The liquid overbased alkali or alkaline earth metal salt of the 1,3-diketone and carboxylic acid prepared in accordance with the process of claim 12.

21. A halogen-containing polymer composition comprising a halogen-containing polymer and a heat-stabilizing amount of the liquid overbased alkali or alkaline earth metal salt of the 1,3-diketone and carboxylic acid prepared in accordance with the process of claim 1.

22. A halogen-containing polymer composition comprising a halogen-containing polymer and a heat-stabilizing amount of the liquid overbased alkali or alkaline earth metal salt of the 1,3-diketone and carboxylic acid prepared in accordance with the process of claim 12.

* * * * *